US007001722B1

(12) United States Patent
Caskey et al.

(10) Patent No.: US 7,001,722 B1
(45) Date of Patent: Feb. 21, 2006

(54) PARALLEL PRIMER EXTENSION APPROACH TO NUCLEIC ACID SEQUENCE ANALYSIS

(75) Inventors: C. Thomas Caskey, Houston, TX (US); John Shumaker, Houston, TX (US); Andres Metspalu, Tartu (EE)

(73) Assignees: Baylor College of Medicine, Houston, TX (US); Pharmacia Biotech AB, Tartu (EE)

( * ) Notice: Subject to any disclaimer, the term of this patent is extended or adjusted under 35 U.S.C. 154(b) by 0 days.

(21) Appl. No.: 09/711,476

(22) Filed: Nov. 13, 2000

Related U.S. Application Data

(63) Continuation of application No. 08/564,100, filed as application No. PCT/US94/07086 on Jun. 22, 1994, now Pat. No. 6,153,379.

(30) Foreign Application Priority Data

Jun. 22, 1993 (SE) ................................. 9302152

(51) Int. Cl.
 *C12Q 1/68* (2006.01)
 *C12P 19/34* (2006.01)
 *C07H 21/02* (2006.01)
(52) U.S. Cl. ..................... 435/6; 435/91.2; 435/91.1; 536/23.1; 536/24.3; 536/24.31; 536/24.33
(58) Field of Classification Search ................. None
See application file for complete search history.

(56) References Cited

U.S. PATENT DOCUMENTS

| 4,689,405 | A |   | 8/1987  | Frank et al.      |         |
|-----------|---|---|---------|-------------------|---------|
| 4,874,492 | A | * | 10/1989 | Mackay            | 204/461 |
| 5,202,231 | A |   | 4/1993  | Drmanac et al.    |         |
| 5,302,509 | A |   | 4/1994  | Cheeseman         |         |
| 5,503,980 | A |   | 4/1996  | Cantor            | 435/6   |
| 5,605,794 | A | * | 2/1997  | Rust et al.       | 435/6   |
| 5,631,134 | A |   | 5/1997  | Cantor            | 435/6   |
| 5,888,819 | A |   | 3/1999  | Goelet et al.     | 435/5   |
| 6,004,744 | A |   | 12/1999 | Goelet et al.     | 435/5   |
| 6,013,431 | A | * | 1/2000  | Soderlund et al.  | 435/6   |

FOREIGN PATENT DOCUMENTS

| EP | 0 412 883 B1  | 2/1991  |
|----|---------------|---------|
| WO | WO 89/10977   | 11/1989 |
| WO | WO 90/04652   | 5/1990  |
| WO | WO 90/09455   | 8/1990  |
| WO | WO 90/13666   | 11/1990 |
| WO | WO 90/15070   | 12/1990 |
| WO | WO 91/06678   | 5/1991  |
| WO | WO 91/13075   | 9/1991  |
| WO | WO 92/10587   | 6/1992  |
| WO | WO 92/10588   | 6/1992  |
| WO | WO 92/15712   | 9/1992  |
| WO | WO 92/16657   | 10/1992 |
| WO | WO 93/05183   | 3/1993  |
| WO | WO 93/13220   | 7/1993  |
| WO | WO 93/17126   | 9/1993  |
| WO | WO 93/21340   | 10/1993 |
| WO | WO 95/15970   | 6/1995  |

OTHER PUBLICATIONS

Sokolov, B. P., "Primer extension technique for the detection of single nucleotide in genomic DNA," *Nucleic Acids Research*, 18(12) :3671 (1990).
Delius H. et al., "Separation of complementary strands of plasmid DNA using the biotin-avidin system and its application to heteroduplex formation and RNA/DNA hybridization in electron microscopy," *Nucleic Acid Research*, 13(15) : 5457-5469 (1985).
Kuppuswamy, M. N. et al., "Single nucleotide primer extension to detect genetic diseases: Experimental application to hemophilia B (factor IX) and cystic fibrosis genes," *Proc. Natl. Acad. Sci. USA*, 88:1143-1147 (1991).
Nyren', P. et al., "Solid Phase DNA Minisequencing by an Enzymatic Luminometric Inorganic Pyrophosphate Detection Assay," *Anal. Biochemistry*, 208:171-175 (1993).
Cotton, R.G.H., "Current methods of mutation detection," *Mutation Research*, 285:125-144 (1993).
Kornher J. S. et al., "Mutation Detection Using Nucleotide Analogs that alter electrophoretic Mobility," *Nucleic Acids Research*, 17 : (19) 7779-7784 (1989).
Lee, Jin-Sung et al., "Identification of the most common mutation within the porphobilinogen deaminase gene in Swedish patients with acute intermittent porphyria," *Proc. Natl. Acad. Sci. USA*, 88:10912-10915 (1991).

(Continued)

*Primary Examiner*—Jeffrey Fredman
(74) *Attorney, Agent, or Firm*—Hamilton, Brook, Smith & Reynolds, P.C.

(57) ABSTRACT

A method of analyzing a polynucleotide of interest, comprising providing one or more sets of consecutive oligonucleotide primers differing within each set by one base at the growing end therof; annealing a single strand of the polynucleotide or a fragment of the polynucleotide to the oligonucleotide primers under hybridization conditions; subjecting the primers to single base extension reactions with a polymerase and terminating nucleotides, the terminating nucleotides being mutually distinguishable; and observing the location and identity of each terminating nucleotide to thereby analyze the sequence or a part of the nucleotide sequence of the polynucleotide of interest, is disclosed. An apparatus comprising a solid support to which is attached at defined locations thereon one or more sets of consecutive oligonucleotide primers differing within each set by one base at the growing end thereof is also described.

12 Claims, 6 Drawing Sheets

OTHER PUBLICATIONS

Chemical Abstracts,113 (25) : 161 (1990) , Edwards, A. et al., "Automated DNA sequencing of the human HPRT locus," *Genomics*, 6(4) :593-608 (1990).

Chemical Abstracts, 117 (23) :645 (1992) , Monnat, R.J. et al., "Nucleotide sequence analysis of human hypoxanthine phosphoribosyltransferase (HPRT) gene deletions," *Genomics*, 13(3) :777-787 (1992).

Chemical Abstracts,104(25) :161 (1986) Kim, S. H. et al., "The organization of the human HPRT gene," *Nucleic Acids Res.*, 14(7) :3103-3118 (1986).

Khrapko, K.R. et al., "A method for DNA sequencing by hybridazaiton with oligonucleotide matrix," *DNA Sequence-DNA Sequencing and Mapping*, 1(3) :375-388 (1991).

Kharpko, K.R. et al., "An oligonucleotide hybridization approach to DNA sequencing," *FEBS Ltrs.*, 256(1,2) :188-122 (1989).

Barinaga, M., "Will 'DNA Chip' Speed Genome Initiative," *Science*, pp. 253 (1991).

Kostichka, A. J., "High Speed Automated DNA Sequencing In Ultrathin Slab Gels," *Biotechnology*, 10:78-81 (1992).

Krook, Anna, et al., "Rapid and simultaneous detection of multiple mutations by pooled and multiplex single nucleotide primer extension: application to the study of insulin-responsive glucose transporter and insulin receptor mutations in non-insulin-dependent diabetes," *Hum. Mol. Genet..* 1(6): 391-395 (1992).

* cited by examiner

REGION OF INTEREST

| GATAGCAATC | GCTTACGGTA | ATCCGGCCTG |
| CTATCGTTAG | CGAATGCCAT | TAGGCCGGAC |

SENSE PRIMERS

5'-GATAGCAATC-3'
   ATAGCAATCG
    TAGCAATCGC
     AGCAATCGCT
      GCAATCGCTT
       CAATCGCTTA
        AATCGCTTAC
         ATCGCTTACG
          TCGCTTACGG
           CGCTTACGGT

ANTI-SENSE PRIMERS

3'-GAATGCCATT-5'
   AATGCCATTA
    ATGCCATTAG
     TGCCATTAGG
      GCCATTAGGC
       CCATTAGGCC
        CATTAGGCCG
         ATTAGGCCGG
          TTAGGCCGGA
           TAGGCCGGAC

PARALLEL PRIMER EXTENSION APPROACH TO NUCLEIC ACID SEQUENCE ANALYSIS

RELATED APPLICATIONS

This application is a Continuation of U.S. application Ser. No. 08/564,100, filed Mar. 6, 1998, now U.S. Pat. No. 6,153,379, which is the U.S. National Phase Application of PCT/US94/07086, filed Jun. 22, 1994, which is a Continuation-in-Part Application of Sweden Application No. SE 9302152-5, filed on Jun. 22, 1993. The entire teachings of the of above applications are incorporated herein by reference.

GOVERNMENT FUNDING

This invention was made with Government Support under grant number 5-R01-DK31 428-11 awarded by the National Institutes of Health. The United States Government has certain rights in the invention.

BACKGROUND OF THE INVENTION

Today, there are two predominant methods for DNA sequence determination: the chemical degradation method (Maxam and Gilbert, *Proc. Natl. Acad. Sci.*, 74:560–564 (1977), and the dideoxy chain termination method (Sanger et al., *Proc. Natl. Acad. Sci.*, 74:5463–5467 (1977)). Most automated sequencers are based on the chain termination method utilizing fluorescent detection of product formation. There are two common variations of these systems: (1) dye-labeled primers to which deoxynucleotides and dideoxynucleotides are added, and (2) primers to which deoxynucleotides and fluorescently labeled dideoxynucleotides are added. In addition, the labeled deoxynucleotides can be used in conjunction with unlabeled dideoxynucleotides. This method is based upon the ability of an enzyme to add specific nucleotides onto the 3' hydroxyl end of a primer annealed to a template. The base pairing property of nucleic acids determines the specificity of nucleotide addition. The extension products are separated electrophoretically on a polyacrylamide gel and detected by an optical system utilizing laser excitation.

Although both the chemical degradation method and the dideoxy chain termination method are in widespread use, there are many associated disadvantages: for example, the methods require gel-electrophoretic separation. Typically, only 400–800 base pairs can be sequenced from a single clone. As a result, the systems are both time- and labor-intensive. Methods avoiding gel separation have been developed in attempts to increase the sequencing throughput.

Methods have been proposed by Crkvenjakov (Drmanac et al., *Genomics*, 4:114 (1989); Strezoska et al., (*Proc. Natl. Acad. Sci. USA*, 88:10089 (1991); Drmanac et al., *Science*, 260: 1649 (1991)) and Bains and Smith (Bains and Smith, J., *Theoretical Biol.*, 135: 303 (1988)). These sequencing by hybridization (SBH) methods potentially can increase the sequence throughput because multiple hybridization reactions are performed simultaneously. This type of system utilizes the information obtained from multiple hybridizations of the polynucleotide of interest, using short oligonucleotides to determine the nucleic acid sequence (Drmanac, U.S. Pat. No. 5,202,231). To reconstruct the sequence requires an extensive computer search algorithm to determine the optimal order of all fragments obtained from the multiple hybridizations.

These methods are problematic in several respects. For example, the hybridization is dependent upon the sequence composition of the duplex of the oligonucleotide and the polynucleotide of interest, so that GC-rich regions are more stable than AT-rich regions. As a result, false positives and false negatives during hybridization detection are frequently present and complicate sequence determination. Furthermore, the sequence of the polynucleotide is not determined directly, but is inferred from the sequence of the known probe, which increases the possibility for error. A great need remains to develop efficient and accurate methods for nucleic acid sequence determination.

SUMMARY OF THE INVENTION

The current invention pertains to methods for analyzing, and particularly for sequencing, a polynucleotide of interest, and an apparatus useful in analyzing a polynucleotide of interest. In one embodiment of the current invention, the nucleotide sequence of a polypeptide of interest is analyzed for the presence of mutations or alterations. In a second embodiment of the current invention, the nucleotide sequence of a polypeptide of interest, for which the nucleotide sequence was not known previously, is determined. The method comprises detecting single base extension events of a set of specific oligonucleotide primers, such that the label and position of each separate extension event defines a base in a polynucleotide of interest.

In one method of the current invention, a solid support is provided. An array of a set or several sets of consecutive oligonucleotide primers of a specified size having known sequences is attached at defined locations to the solid support. The oligonucleotide primers differ within each set by one base pair. The oligonucleotide primers either correspond to at least a part of the nucleotide sequence of one strand of the polynucleotide of interest, if the sequence is known, or represent a set of all possible nucleotide sequences for oligonucleotide primers of the specified size, if the sequence is not known. A polynucleotide of interest, which may be DNA or RNA, or a fragment of the polynucleotide of interest, is annealed to the array of oligonucleotide primers under hybridization conditions, thereby generating "annealed primers." The annealed primers are subjected to single base extension reaction conditions, under which a nucleic acid polymerase and terminating nucleotides, such as dideoxynucleotides (ddNTPs) corresponding to the four known bases (A, G, T and C), are provided to the annealed primers. The terminating nucleotides can also comprise a terminating string of known polynucleotides, such as dinucleotides. As a result of the single base extension reaction, extended primers are generated, in which a terminating nucleotide is added to each of the annealed primers. The terminating nucleotides can be provided to the annealed primers either simultaneously or sequentially. The terminating nucleotides are mutually distinguishable; i.e., at least one of the nucleotides is labeled to facilitate detection. After addition of the terminating nucleotides, the sequence of the polynucleotide of interest is analyzed by "reading" the oligonucleotide array: the identity and location of each terminating nucleotide within the array on the solid support is observed. The label and position of each terminating nucleotide on the solid support directly defines the sequence of the polynucleotide of interest that is being analyzed.

In a second method of the current invention, the polynucleotide of interest is analyzed for the presence of specific mutations through the use of oligonucleotide primers that are not attached to a solid support. The oligonucleotide primers are tailored to anneal to the polynucleotide of interest at a point immediately preceding the mutation site(s). If more than one mutation site is examined, the oligonucleotide primers are designed to be mutually distinguishable: in a preferred embodiment, the oligonucleotide primers have different mobilities during gel electrophoresis. For example, oligonucleotides of different lengths are used. After the oligonucleotide primers are annealed to the polynucleotide of interest, the annealed primers are subjected to single base extension reaction conditions, resulting in extended primers in which terminating nucleotides are added to each of the annealed primers. As in the first method of the current invention, the terminating nucleotides are mutually distinguishable. After addition of the terminating nucleotides, the sequence of the polynucleotide of interest is analyzed by elating the extended primers, performing gel electrophoresis, and "reading" the gel: the identity and location of each terminating nucleotides on the gel is observed using standard methods, such as with an automated DNA sequencer. The label and position of each terminating nucleotide on the gel directly defines the sequence of the polynucleotide of interest that is being analyzed, and indicates whether a mutation is present.

The apparatus of the current invention comprises a solid support having an array of one or more sets of consecutive oligonucleotide primers with known sequences attached to it at defined locations, each oligonucleotide primer differing within each set by one base pair. The set of oligonucleotide primers either corresponds to at least a part of the nucleotide sequence of one strand of the polynucleotide of interest, if the sequence is known, or represents all possible nucleotide sequences for oligonucleotide primers of the specified size, if the sequence is not known.

The current invention provides both direct information, due to the detection of a specific nucleotide addition, and indirect information, due to the known sequence of the annealed primer to which the specific base addition occurred, for the polynucleotide of interest. The ability to determine nucleic acid sequences is a critical element of understanding gene expression and regulation. In addition, as advances in molecular medicine continue, sequence determination will become a more important element in the diagnosis and treatment of disease.

BRIEF DESCRIPTION OF THE DRAWINGS

FIG. 1 depicts an example of a set of oligonucleotide primers (sense primers, SEQ ID NOS: 2–11, antisense primers, SEQ ID NOS: 12–21), comprising consecutive primers differing by one base pair at the growing end and capable of hybridizing successively along the relevant part(s) or the whole of the polynucleotide of interest (SEQ ID NOS: 1 and 22).

DETAILED DESCRIPTION OF THE INVENTION

Figures 2, 3, 4:
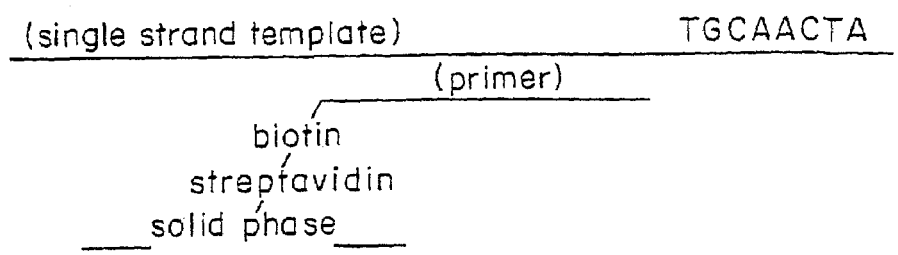
FIG. 2 is a schematic illustration of a single strand template bound to a primer which is in turn attached to a solid support.
FIG. 3 illustrates a set of consecutive oligonucleotide primers for a part of the polynucleotide of interest following immediately after the primer illustrated in FIG. 2.
FIG. 4 illustrates the single base pair additions to all the primers illustrated in FIG. 3, as well as the corresponding additions for the corresponding primers related to the complementary strand of the polynucleotide of interest.

The current invention pertains to methods for analyzing the nucleotide sequence of a polynucleotide of interest. The method comprises hybridizing all or a fragment of a polynucleotide of interest to oligonucleotide primers, conducting single base extension reactions, and detecting the single base extension events. The method can be used to analyze the sequence of a polypeptide of interest by examining the sequence for the presence of mutations or alterations in the nucleotide sequence, or by determining the nucleotide sequence of a polypeptide of interest.

As used herein, the term "polynucleotide of interest" refers to the particular polynucleotide for which sequence information is wanted. Representative polynucleotides of interest include oligonucleotides, DNA or DNA fragments, RNA or RNA fragments, as well as genes or portions of genes. The polynucleotide of interest can be single- or double-stranded. The term "template polynucleotide of interest" is used herein to refer to the strand which is analyzed, if only one strand of a double-stranded polynucleotide is analyzed, or to the strand which is identified as the first strand, if both strands of a double-stranded polynucleotide are analyzed. The term, "complementary polynucleotide of interest" is used herein to refer to the strand which is not analyzed, if only one strand of a double-stranded polynucleotide is analyzed, or to the strand which is identified as the second strand (i.e., the strand that is complementary to the first (template) strand), if both strands of a double-stranded polynucleotide are analyzed. Either one of the two strands can be analyzed. In a preferred embodiment, both strands of a double-stranded polynucleotide of interest are analyzed in order to verify sequence information obtained from the template (first) strand by comparison with the complementary (second) strand. Nevertheless, it is not always necessary to analyze both strands. For example, if the polynucleotide of interest is being analyzed for the presence of a single base mutation, and not for the complete base sequence in the mutation region, it is sufficient to analyze a single strand of the polynucleotide of interest.

The methods of the current invention can be used to identify the presence of mutations or alterations in the nucleotide sequence of a polypeptide of interest. To identify mutations or alterations, the sequence of the polynucleotide of interest is compared with the sequence of the native or normal polynucleotide. An "alteration" in the polynucleotide of interest, as used herein, refers to a deviation from the expected sequence (the sequence of the native or normal polynucleotide), including deletions, insertions, point mutations, frame-shifts, expanded oligonucleotide repeats, or other changes. The portion of the polynucleotide of interest that contains the alteration is known as the "altered" region. The methods can also be used to determine the polynucleotide sequence of a polypeptide of interest having a previously unknown nucleotide sequence.

In one embodiment of the current invention, the polynucleotide of interest is analyzed by annealing the polynucleotide to an array comprising sets of oligonucleotide primers. The oligonucleotide primers in the array have a length N, where N is from about 7 to about 30 nucleotides, inclusive, and is preferably from 20 to 24 nucleotides, inclusive. Each oligonucleotide primer within each set differs by one base pair. The oligonucleotide primers can be prepared by conventional methods (see Sambrook et al., *Molecular Cloning: A Laboratory Manual* (2nd Ed, 1989)). The sets of oligonucleotide primers are arranged into an array, such that the position and nucleotide content of each oligonucleotide primer on the array is known.

The size and nucleotide content of the oligonucleotide primers in the array depend on the polynucleotide of interest and the region of the polynucleotide of interest for which sequence information is desired. To analyze a polynucleotide of interest for the presence of alterations, consecutive primers differing by one base pair at the growing end and capable of hybridizing successively along the relevant part(s) or the whole of the polynucleotide are used. An example of such a primer set is shown in FIG. 1. If only one or a few specific positions of the polynucleotide sequence are examined for alterations, the necessary array of oligonucleotide primers covers only the mutation regions, and is therefore small. If the whole or a major part of the polynucleotide of interest is to be analyzed for possible mutations at varying positions, the necessary array is larger. For example, the whole hypoxanthine-guanine phosphoribosyltransferase (HPRT) gene can be covered by 900 primers, arranged in a 30×30 array; the whole p53 gene requires 700 primers. If both strands of a double-stranded polynucleotide of interest are analyzed for the presence of alterations, the array comprises consecutive oligonucleotide primers for the suspected mutation region of both the template polynucleotide of interest and the complementary polynucleotide of interest. If the polynucleotide of interest has not been sequenced previously, the array includes oligonucleotide primers comprising all possible N-mers.

The array of sets of oligonucleotide primers is immobilized to a solid support at defined locations (i.e., known positions). The immobilized array is referred to as a "DNA chip," which is the apparatus of the current invention. The solid support can be a plate or chip of glass, silicon, or other material. The solid support can also be coated, such as with gold or silver. Coating may facilitate attachment of the oligonucleotide primers to the surface of the solid support. The oligonucleotide primers can be bound to the solid support by a specific binding pair, such as biotin and avidin or biotin and streptavidin. For example, the primers can be provided with biotin handles in connection with their preparation, and then the biotin-labeled primers can be attached to a streptavidin-coated support. Alternatively, the primers can be bound by a linker arm, such as a covalently bonded hydrocarbon chain, such as a $C_{10-20}$ chain. The primers can also be bound directly to the solid support, such as by epoxide/amine coupling chemistry (see Eggers, M. D. et al., Advances in DNA sequencing Technology, SPIE conference proceedings, Jan. 21, 1993). The solid support can be reused, as described in greater detail below.

In another embodiment of the invention, the polynucleotide of interest is analyzed by annealing the polynucleotide to one or more specific oligonucleotide primers that are not attached to a solid support; such oligonucleotide primers are referred to herein as "free oligonucleotide primers." If free oligonucleotide primers are used, the polynucleotide of interest can be attached to a solid support, such as magnetic beads. The free oligonucleotide primers have a length N, as described above, and are prepared by conventional methods (see Sambrook et al., *Molecular Cloning: A Laboratory Manual* (2nd Ed, 1989)). The size and nucleotide content of the free oligonucleotide primers depend on the polynucleotide of interest and the region of the polynucleotide of interest for which sequence information is desired. To analyze a polynucleotide of interest for the presence of alterations, primers capable of hybridizing immediately adjacent to the relevant part(s) of the polynucleotide are used. If more than one position of the polynucleotide sequence is examined for alterations, the free oligonucleotide primers are mutually distinguishable: i.e., the oligonucleotide primers have different mobilities during gel electrophoresis. In a preferred embodiment, oligonucleotides of different lengths are used. For example, an oligonucleotide primer of 10 nucleotides in length is designed to hybridize immediately adjacent to one putative mutation, and an oligonucleotide primer of 12 nucleotides in length is designed to hybridize immediately adjacent to a second putative mutation. Because the oligonucleotide primers are of different lengths, they will migrate to different positions on the gel. Thus, in this manner, the nucleotide content of each oligonucleotide primer can be identified by the position of the oligonucleotide primer on the gel.

The polynucleotide of interest is hybridized to the array of oligonucleotide primers, or to the free nucleotide primers, under high stringency conditions, so that an exact match between the polynucleotide of interest and the oligonucleotide primers is obtained, without any base-pair mismatches (see Sambrook et al., *Molecular Cloning: A Laboratory Manual* (2nd Ed, 1989)). For example, a schematic illustration of a hypothetical polynucleotide of interest annealed to an oligonucleotide primer that is attached to a solid support is shown schematically in FIG. 2. In FIG. 2, a part of the sequence of the polynucleotide of interest that follows immediately after the portion of the polynucleotide that is bound to the oligonucleotide primer on the array is shown as TGCAACTA. Six corresponding consecutive primers are shown in FIG. 3, i.e. primers ending with the pairing bases A, AC, ACG, etc. If the polynucleotide of interest is double-stranded, it can be separated into two single strands either before or after the binding of the polynucleotide of interest to the array oligonucleotide primers. Both the template and the complementary polynucleotide of interest can be analyzed utilizing a single array. Thus, while not shown in FIG. 2, appropriate primers corresponding to the complementary polynucleotide of interest are also attached to the solid support in known positions.

When the polynucleotide of interest is hybridized to the array of sets of oligonucleotide primers, or to the free oligonucleotide primers, under hybridization conditions, annealed primers are formed. The term, "annealed primer," as used herein, refers to an oligonucleotide primer (either free or attached to a solid support) to which a polynucleotide of interest is hybridized. The annealed primers are subjected to a single base extension reaction. The "single base extension reaction," as used herein, refers to a reaction in which the annealed primers are provided with a reaction mixture comprising a DNA polymerase, such as T7 polymerase, and terminating nucleotides under conditions such that single terminating nucleotides are added to each of the annealed primers. The term "terminating nucleotides," as used herein, refers to either single terminating nucleotides, or units of nucleotides, the units preferably being dinucleotides. In a preferred embodiment, the terminating nucleotides are single dideoxynucleotides. The terminating nucleotides can comprise standard nucleotides, and/or nucleotide analogues. The terminating nucleotide added to each annealed primer is thus a base pairing with the template base on the polynucleotide of interest, and is added immediately adjacent to the growing end of the respective primer. An oligonucleotide primer to which a terminating nucleotide has been added through the single base extension reaction is termed an "extended primer." Thus, as schematically shown for both strands of the hypothetical polynucleotide of interest in FIG. 4, a single nucleotide is added to each primer in the array; the primer set related to the strand illustrated in FIG. 2 is shown to the left in FIG. 4, and the other (complementary) strand is shown to the right. The nucleotides added are shown in extra bold type.

The terminating nucleotides preferably comprise dNTPs, and particularly comprise dideoxynucleotides (ddNTPs), but other terminating nucleotides apparent to the skilled person can also be used. If the terminating nucleotides are single nucleotides, then nucleotides corresponding to each of the four bases (A, T, G and C) are utilized in the single base extension reaction. If the terminating nucleotides are dinucleotide units, for example, then nucleotides corresponding to each of the sixteen possible dinucleotides are utilized.

The nucleotides are mutually distinguishable. For example, if the solid support is coated with a free electron metal, such as with gold or silver, surface plasmon resonance (SPR) microscopy allows identification of each nucleotide, by the change of the refractive index at the surface caused by each base extension. Alternatively, at least one of the terminating nucleotides is labeled by standard methods to facilitate detection. Suitable labels include fluorescent dyes, chemiluminescence, and radionuclides. The number of nucleotides that are labeled can be varied. It is sufficient to use three labeled terminating nucleotides, the fourth terminating nucleotide being identified by its "non-label," if single nucleotides are added in the base extension reaction. For example, if one is examining the polynucleotide of interest for the presence of a particular alteration, and not for the complete base sequence in the altered region, three labeled terminating nucleotides are sufficient. Fewer than three labels can also be utilized under appropriate circumstances. An exemplification of the use of two labeled and two unlabelled dNTPs is described below. If a specific alteration is to be investigated, such as a point mutation, only the native or normal nucleotide need be labeled, as a mutation would be indicated by the presence of the "non-label." Alternatively, the expected mutant nucleotide can also be labeled.

After the single base extension reaction has been performed, the identity and location of each terminating nucleotide is observed. If free oligonucleotide primers are used, the extended primers are eluted and separated by gel electrophoresis, and the gel is then analyzed. If oligonucleotide primers attached to an array are used, the array itself is analyzed. The gel or array is analyzed by detecting the labeled, terminating nucleotides bound to the oligonucleotide primers. The labeled, terminating nucleotides are detected by conventional methods, such as by an optical system. For example, a laser excitation source can be used in conjunction with a filter set to isolate the fluorescence emission of a particular type of terminating nucleotide. Either a photomultiplier tube, a charged-coupled device (CCD), or another suitable fluorescence detection method can be used to detect the emitted light from fluorescent terminating nucleotides.

The sequence of the polynucleotide of interest can be analyzed from the label pattern observed on the array or on the gel, since the position of each different primer on the array or on the gel is known, and since the identity of each terminating nucleotide can be determined by its specific label. The label and position of each terminating nucleotide either within the array or on the gel will directly define the sequence of the polynucleotide of interest that is being analyzed. Mutations or alterations in the sequence of the polynucleotide of interest are indicated by alterations in the expected label pattern. For example, assume that the nucleotide sequence shown in FIG. 2 contains a mutation: the third base C from the left is replaced by a G in the polynucleotide of interest. The top primer in FIG. 3 will still be extended by a C as shown in FIG. 4, whereas the next primer will be extended by a C rather than a G. Since this new, unexpected base C can be identified by its specific label and the respective primer location is known, the corresponding base mutation is identified as G.

The following simple example illustrates the ability to obtain complete sequence information and to identify a mutation in a representative polynucleotide of interest. The example utilizes two labeled terminating nucleotides, which give complete sequence information.

Assume a normal polynucleotide of the following base pair composition:

+ A C T G C T T A G

− T G A C G A A T C and a corresponding mutant polynucleotide having the following base pair composition, which has a single base mutation in the third base pair:

+ A C C G C T T A G

− T G G C G A A T C.

Using fluorescent labeling, for example, with a red label ("R") for terminating A and a green label ("G") for terminating G, and no label, i.e., null ("N") for the remaining bases T and C, the following "binary" codes allowing sequence interpretation would be obtained for the normal, mutant and heterozygote sequences, respectively:

+ N-G-R-N-G-R-R-N-N    Normal

− R-N-N-G-N-N-N-R-G

+ N-G-G-N-G-R-R-N-N    Mutant (Affected)

− R-N-N-G-N-N-N-R-G

R

+ N-G-G-N-G-R-R-N-N    Heterozygote (Carrier)

− R-N-N-G-N-N-N-R-G.

The presence of such a point mutation will affect the base pairing of the next few oligonucleotide primers to the polynucleotide of interest, and thereby the primer extensions obtained, such that the bases in the vicinity of the mutation (i.e., in the altered region) may not be accurately identified. To optimize identification of bases in the altered region, it is preferred to analyze both strands of such a double-stranded polynucleotide of interest. The few bases that may be difficult to identify on the template polynucleotide of interest, as well as the changed base, will be identified by the base extensions of the primers for the complementary polynucleotide of interest, as the analysis of the complementary polynucleotide of interest approaches the mutation site from the opposite direction. In the nearest regions on either side of the alteration, the sequence determination is thereby provided by the oligonucleotide primers for one of the two strands.

The sequence of a polynucleotide of interest for which the sequence is previously known can be determined using methods similar to those described above in reference to identification of mutations utilizing an array of oligonucleotide primers. As before, the positions of the terminating nucleotides within the array will directly define the sequence position of each nucleotide in the polynucleotide of interest.

To determine the oligonucleotide sequence, one annealed primer is selected to be the "starting" annealed primer; it is supposed for purposes of analysis that the sequence of the polynucleotide of interest "starts" with this primer. The nucleotide which has been added to the starting annealed primer is detected using standard methods. Then, a second annealed primer which has the same nucleotide sequence as the starting annealed primer, minus the 5' nucleotide and with the addition of the added nucleotide, is then selected. The terminating nucleotide which has been added to the second annealed primer is detected. These steps are then repeated, using the second annealed primer as the "starting" annealed primer in each repetition, until the sequence of the polynucleotide of interest is determined. For example, if the oligonucleotide primers are 10 nucleotides in length (N=10), the starting annealed primer is chosen to correspond to the first ten bases of the sequence. The terminating nucleotide of the starting annealed primer is then determined. Next, bases 2–11 (i.e., bases 2–10 of the starting annealed primer plus the terminating nucleotide extension) are matched to another annealed primer. This primer is the second annealed primer. The terminating nucleotide of the second annealed primer is then determined. These steps are repeated to determine the complete sequence. In this manner, the single base extension reaction automatically links together the set of annealed primers.

After analysis of the nucleotide sequence of a polypeptide of interest, the polynucleotide of interest and the terminating nucleotides can be removed from the DNA chip, so that the chip can be reused. In a preferred embodiment, the added terminating nucleotides are capable of being removed from the solid support after analysis of the polynucleotide of interest has been completed. Once the nucleotides are removed, the solid support with the immobilized oligonucleotide primers can be used for a new analysis. The nucleotides can be removed using standard methods, such as enzymatic cleavage or chemical degradation. Enzymatic cleavage, for example, would use a terminating nucleotide which can be removed by an enzyme. The single base extension reaction could result in addition to the oligonucleotide primers of RNA dideoxyTTP or RNA dideoxyCTP by reverse transcriptase or other polymerase. A C/T cleavage enzyme, such as RNase A, can then be used to "strip" off the RNA dideoxynucleotides. Alternatively, sulfur-containing dideoxy-A or dideoxy-G can be used during the single extension reaction; a sulfur-specific esterase, which does not cleave phosphates can then be used to cleave off the dideoxynucleotides. For chemical degradation, a chemically degradable terminating nucleotide can be used. For example, a modified ribonucleotide having its 2'- and 3'-hydroxyl groups esterified, such as by acetyl groups, can be used. After binding of the terminating nucleotide to the annealed primer, the acetyl groups are removed by treatment with a base to expose the 2'- and 3'-hydroxyl groups. The ribose residue can then be degraded by periodate oxidation, and the residual phosphate group removed from the annealed primer by treatment with a base and alkaline phosphatase.

The method and apparatus of the current invention have uses in detecting mutations, deletions, expanded oligonucleotide repeats, and other genetic abnormalities. For example, the current invention can be used to identify frame shifting mutations caused by insertions or deletions. Furthermore, carrier status of heritable diseases, such as cystic fibrosis, β-thalassemia, α-1, Gaucher's disease, Tay Sach's disease, or Lesch-Nyham syndrome, can be easily determined using the current invention, because both the normal and the altered signals would be detected. Furthermore, mixtures of DNA molecules such as occur in HIV infected patients with drug resistance can be determined. The HIV virus may develop resistance against drugs like AZT by point mutations in the nucleotide sequence of a reverse transcriptase (RT) gene. When mutated viruses start to appear in the virus population, both the mutated gene and the normal (wild type) gene can be detected. The greater the proportion is of the mutant, the greater is the signal from the corresponding mutant terminating nucleotide.

The current invention is further exemplified by the following Examples.

EXAMPLE 1

Analyzing the Sequence of a Polynucleotide of Interest Utilizing Free Oligonucleotide Primers An analysis of the hypoxanthine-guanine phosphoribosyltransferase (HPRT) gene (the polypeptide of interest) was conducted for three individuals (Patients A, B, and C).

A. Obtaining the Polynucleotide of Interest

The polymerase chain reaction (see Sambrook et al., *Molecular Cloning. A Laboratory Manual* (2nd Ed, 1989), especially Chapter 14) was utilized to amplify the polynucleotide of interest. During the reaction, one of the two PCR primers was tagged with a biotin group. Following amplification, the single strand template was captured with streptavidin coated magnetic beads. For a 50 μl PCR reaction, 25 μl of Dynal M-280 paramagnetic beads (Dynal A/S, Oslo, Norway) was used. The supernatant of the beads was removed and replaced with 50 μl of a binding and washing buffer (10 mM Tris-HCl (pH 7.5); 1 mM EDTA; 2 M NaCl). The PCR product was added to the beads and incubated at room temperature for 30 minutes for bead capture of the products. The single stranded polynucleotide of interest was isolated by the addition of 150 μl of 0.15 M NaOH for 5 minutes. The beads were captured, the supernatant was removed, and 150 μl of 0.15 M NaOH was again added for five minutes. Following denaturation, the beads were washed once with 150 μl of 0.15 M NaOH and twice with 1×T7 annealing buffer (40 mM Tris-HCl (pH 7.5); 20 mM $MgCl_2$; 50 mM NaCl). The beads were finally suspended in 70 μl of water. This process both isolates the single-stranded polynucleotide of interest and removes any unincorporated dNTPs remaining after PCR.

B. Analyzing the Sequence of the Polynucleotide of Interest

Figure 5:
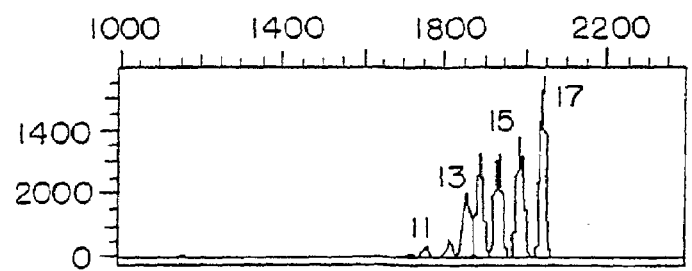
FIG. 5 is a graphic depiction of the length of extended primers formed utilizing free oligonucleotide primers annealed to a polynucleotide of interest.

After single strand isolation, the oligonucleotide primers were annealed to the polynucleotide of interest by heating to 65° C. for approximately two minutes and cooling to room temperature over approximately 20 minutes. The 10 μl reaction volume consisted of 7 μl of the polynucleotide of interest (0.5–1 pmol), 2 μl of 5×T7 annealing buffer, and 1 μl of extension primer (3–9 pmol). The extension reaction was then performed. For the reaction, 1 μl of DTT, 2 μl of T7 polymerase (diluted 1:8) and 1 μl of ddNTPs (final concentration of 0.5 uM) were added. The reaction proceeded at 37° C. for two minutes, and then was stopped by the addition of 100 μl of washing buffer (1×SSPE, 0.1% SDS, 30% ethanol). The beads were washed twice with 150 μl of the washing buffer. The extension products were eluted by the addition of 5 μl of formamide and heated to 70° C. for two minutes. The beads were captured by the magnet and the supernatant containing the extension products was collected and analyzed on a ABI 373 (Applied Biosystems, Inc.). Oligonucleotide primers of lengths varying from 10 to 17 were used. As shown in FIG. 5, extension products were formed efficiently.

1. Deoxynucleotide Labeling—Four Fluorophores

Each ddNTP was labeled by a different fluorophore. ABI Dye Terminator dyes designed for taq polymerase were used: ddG is blue, ddA is green, ddT is yellow, and ddC is red. Four fluorescent ddNTPs were added to each reaction tube. The extension products were purified, gel separated, and analyzed on an ABI 373. Two different bases of exon 3 of the HPRT gene were analyzed: base 16534 (wild type is A) and base 16620 (wild type is C).

Figure 6A:
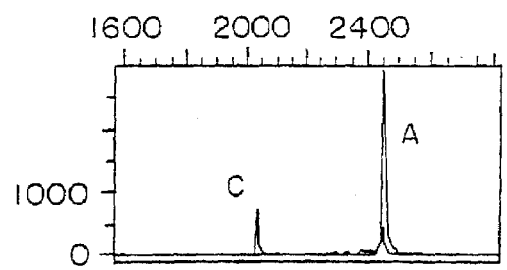
FIGS. 6A, 6B and 6C are graphic depictions of electrophoretograms demonstrating the detection of the presence of a mutation in a polynucleotide of interest.
Figure 6B:
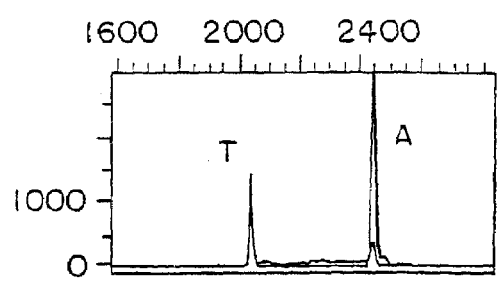
Figure 6C:
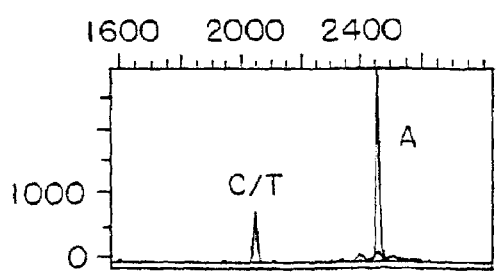

The results of the four fluor, single lane, indicated that the presence of mutations could be identified easily. All three patients are wild type for A at base 16534 (data not shown). Electrophoretograms shown in FIGS. 6A, 6B and 6C indicate that Patient A is wild type (C) at base 16620 (FIG. 6A), patient B is a mutated individual (C-->T) at base 16620 (FIG. 6B), and patient C is a carrier at base 16620 (both C and T) (FIG. 6C).

2. Deoxynucleotide Labeling—Single Fluorophore

Each ddNTP was labeled by the same fluorophore. DuPont NEN fluorescein dyes (NEL 400–404) were used. Each ddNTP appears blue in the ABI 373. Only one fluorescent ddNTP is added to each reaction tube. The extension products were purified, gel separated, and analyzed on an ABI 373. Four lanes on the gel must be used to analyze each base. Two different bases of exon 3 of the HPRT gene were analyzed: base 16534 (wild type is A) and base 16620 (wild type is C).

The results of the single fluor, four lane, demonstrated results that were identical to those obtained using the four fluor, single lane method described in (1), above. This type of assay minimizes the effect of the fluorophore differences during extension product formation and gel separation.

3. Deoxynucleotide Labeling—Biotinlyated Dideoxynucleotides

The ddNTPs are labeled with a biotin group. Four separate reactions are performed, whereby only one of the four ddNTPs is biotinylated. Following the extension reaction, a strepavidin (or avidin) coupled fluorescent group is attached to the biotinylated ddNTPs. Because the biotin group is small, uniform incorporation of the ddNTPs is expected and base-specific differences in extension are minimized. Furthermore, the fluorescent signal can be amplified because the biotin group can bind a steptavidin moiety coupled to multiple fluors.

EXAMPLE 2

Analyzing the Sequence of a Polynucleotide of Interest Utilizing Labeled Deoxynucleotides An analysis of the hypoxanthine-guanine phosphoribosyltransferase (HPRT) gene (the nucleotide sequence of a polypeptide of interest) was conducted for three individuals (Patients A, B, and C). The third exon of the HPRT gene was examined.

Microscope glass slides were epoxysilanated at 80° C. for eight hours using 25% 3' glycidoxy propyltriethoxysilane (Aldrich Chemical) in dry xylene (Aldrich Chemical) with a catalytic amount of diisopropylehylamine (Aldrich Chemical), according to Southern (Nucl. Acids Res. 20:1679 (1992), and Genomics 13:1008 (1992)). The DNA chips were made by placing 0.5 μl drops of 5'-amino-linked oligonucleotides (50 μM, 0.1 M NaOH) at 37° C. for six hours in a humid environment. The chips were washed in 50° C. water for 15 minutes, dried and used. The annealing reaction consisted of adding 2.2 μl of single-stranded DNA (0.1 μM in T7 reaction buffer) to each grid position, heating the chip in a humid environment to 70° C. and then cooling slowly to room temperature. A 1 μl drop of 0.1 M DTT, 3 units of Sequenase Version 2.0 (USB), 5 μCi α-$^{32}$P dNTP (3000 Ci/mmol) (DuPont NEN) and noncompeting unlabeled 18.5 μM ddNTPs (Pharmacia) were added to each grid position for three minutes. The reaction was stopped by washing in 75° C. water, and analyzed on a Phosphorimager (Molecular Dynamics).

Figure 7A:
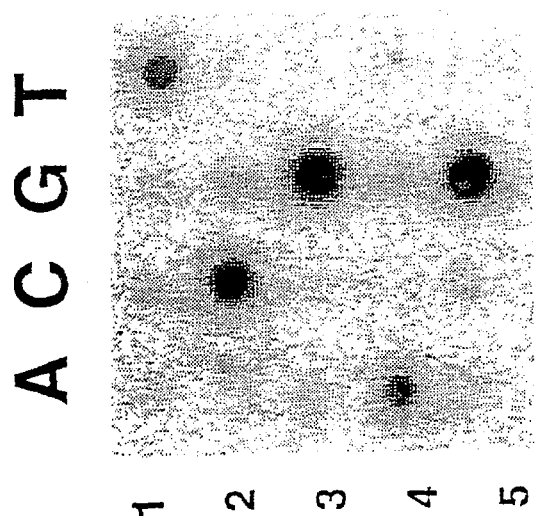
FIGS. 7A, 7B and 7C depict the results of a DNA chip-based analysis for a five-base region within the third exon of the HPRT gene.
Figure 7B:
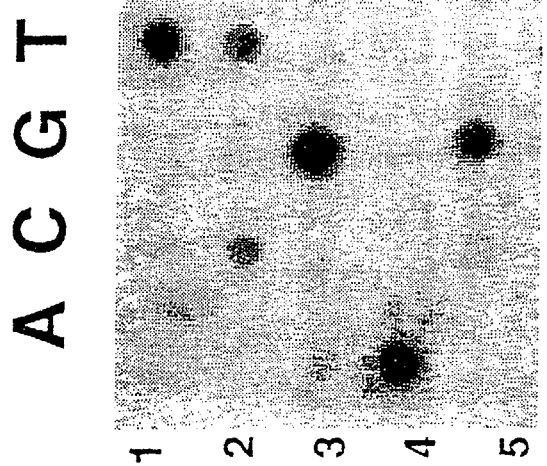
Figure 7C:
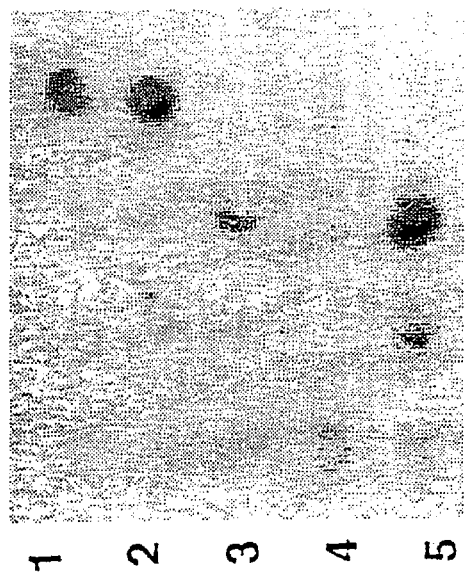

FIGS. 7A, 7B and 7C depict the results of a DNA chip-based analysis for a five-base region within the third exon of the HPRT gene. The rows correspond to a particular base under investigation, and the columns correspond to the labeled base. FIG. 7A demonstrates the wild type sequence (TCGAG), FIG. 7B demonstrates a C-->T mutation, and FIG. 7C demonstrates a C-->T mutation.

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for determining nucleotide identity of at least one nucleotide position of a polynucleotide of interest, comprising the steps of;

a) contacting said polynucleotide of interest with a population of single-stranded primers, wherein said single-stranded primers comprise an array of one or more sets of one or more oligonucleotides, wherein at least one set comprises at least two oligonucleotides that are substantially homologous but differ from each other by one base at their 3' termini, wherein the oligonucleotides of the array have known sequence and wherein each oligonucleotide is attached to a solid support at a known location, to form the array, wherein at least one oligonucleotide of the array hybridizes to said polynucleotide of interest immediately adjacent to each nucleotide position to be identified, generating template-single-stranded primer complexes;

b) subjecting said complexes to a single base extension reaction to extend each annealed primer by a terminating nucleotide, generating extended primers;

c) identifying each terminating nucleotide that has been added to each primer; thereby determining the identity of at least one nucleotide position of a polynucleotide of interest; and d) removing the terminating nucleotides from the annealed primers after completed analysis to prepare the solid support for reuse.

2. A method of analyzing a polynucleotide of interest for the presence or absence of an altered region, comprising the steps of:

a) annealing a single sample of the polynucleotide of interest to an array of n primers of N nucleotides in length, wherein each primer is immobilized to a solid support at a known location, and has known sequence, wherein a first primer of the array comprises 1 to N nucleotides, a second primer of the array comprises nucleotides 2 to N of the first primer plus nucleotide N+1, and the $n^{th}$ primer of the array comprises nucleotides 2 to the last nucleotide of primer n−1 plus nucleotides (N+(n−1)) such that each primer differs from the previous primer in the array by one base at the growing end, and wherein primers of the array are capable of hybridizing successively along the polynucleotide of interest, generating a plurality of annealed primers;

b) subjecting the plurality of annealed primers to a single base extension reaction to extend each annealed primer by addition of a terminating nucleotide to form a plurality of extended primers; and c) observing the identity of each terminating nucleotide added in step b), thereby analyzing the polynucleotide of interest for the presence or absence of an altered region.

3. The method of claim 2, wherein the single base extension reaction comprises subjecting the plurality of annealed primers to a reaction mixture comprising a polymerase and nucleotides corresponding to each of the four bases.

4. The method of claim 3, wherein the nucleotides corresponding to each of the four bases are mutually distinguishable.

5. The method of claims 3, wherein three of the four nucleotides are differently labeled.

6. The method of claim 5, wherein the three differently labeled nucleotides are fluorescently labeled.

7. The method of claim 2, further comprising analyzing a polynucleotide that is complementary to the polynucleotide of interest.

8. The method of claim 2, wherein the terminating nucleotides are dideoxynucleotides.

9. The method of claim 2, wherein N is between 7 and 30 inclusive.

10. The method of claim 2, wherein N is between 20 and 24 inclusive.

11. The method of claim 2, wherein observing the identity and location of the terminating nucleotides comprises use of a charge coupled device or a photomultiplier tube.

12. The method of claim 2, wherein the terminating nucleotides are dinucleotides.

* * * * *

SEQUENCE LISTING

<160> NUMBER OF SEQ ID NOS: 9

<210> SEQ ID NO 1
<211> LENGTH: 435
<212> TYPE: DNA
<213> ORGANISM: Helicobacter pylori

<400> SEQUENCE: 1
atgaaaacat ttgaaatttt aagacatttg caagcggatg cgatcgtgtt gtttatgaaa      60
gtgcataact tccattggaa tgtgaaaggc accgattttt tcaatgtgca taaagccact     120
gaagaaattt atgaagagtt tgcggacatg tttgatgatc tcgctgaaag gatcgttcaa     180

```
ttaggacacc accccttagt gactttatct gaagcactca aactcactcg tgtgaaagaa    240
gaaactaaaa cgagcttcca ctctaaagac atctttaaag aaattctagg cgattacaaa    300
cacctagaaa aagaattaa agagctttct aacactgctg aaaagaagg cgataaagtc      360 accgtaactt atgcggacga tcaattggcc aagttgcaaa atccatttg gatgctagaa     420 gctcatttgg cttaa                                                    435
```

<210> SEQ ID NO 2
<211> LENGTH: 144
<212> TYPE: PRT
<213> ORGANISM: Helicobacter pylori

<400> SEQUENCE: 2

```
Met Lys Thr Phe Glu Ile Leu Arg His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Glu Phe Ala
        35                  40                  45

Asp Met Phe Asp Asp Leu Ala Glu Arg Ile Val Gln Leu Gly His His
    50                  55                  60

Pro Leu Val Thr Leu Ser Glu Ala Leu Lys Leu Thr Arg Val Lys Glu
65                  70                  75                  80

Glu Thr Lys Thr Ser Phe His Ser Lys Asp Ile Phe Lys Glu Ile Leu
                85                  90                  95

Gly Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Glu Ala His Leu Ala
    130                 135                 140
```

<210> SEQ ID NO 3
<211> LENGTH: 435
<212> TYPE: DNA
<213> ORGANISM: Helicobacter pylori

<400> SEQUENCE: 3

```
atgaaaacat tgaaattttt aaaacatttg caagcggatg cgatcgtgtt gtttatgaaa     60
gtgcataact tcattggaa cgtgaaaggc accgattttt tcaatgtgca taaagccact     120
gaagaaattt atgaagagtt tgcggacatg tttgatgatc tcgctgaaag gctcgttcaa    180
ttaggacacc accccttagt gactttatct gaagcactca aactcactcg tgtgaaagac    240
gaaactaaaa cgagcttcca ctctaaagac atctttaaag aaattctagg cgattacaaa    300
cacctagaaa aagaattaa agagctttct aacactgctg aaaagaagg cgataaagtc      360 accgtaactt atgcggacga tcaattggcc aagttgcaaa atccatttg gatgctagaa     420 gctcatttgg cttaa                                                    435
```

<210> SEQ ID NO 4
<211> LENGTH: 435
<212> TYPE: DNA
<213> ORGANISM: Helicobacter pylori -continued

```
<400> SEQUENCE: 4
atgaaaacat tgaaattct aaaacatttg caagcggatg cgatcgtgtt atttatgaaa      60
gtgcataact ttcattggaa cgtgaaaggc accgattttt tcaatgtgca taaagccact     120
gaagaaattt atgaagagtt tgcggacatg ttgacgatc tcgctgaaag gatcgttcaa      180
ttagggcatc accccttagt cactttatcc gaagcgatca aactcactcg tgttaaagaa     240
gaaactaaaa cgagcttcca ctctaaagac atctttaaag aaattctaga ggactacaaa    300
tatctagaaa aagaatttaa agagctctct aacaccgctg aaaagaagg cgataaagtt     360 accgtaactt atgcggatga tcaattagcc aagttgcaaa atccatttg gatgctgcaa     420 gcccatttgg cttaa                                                      435
```

<210> SEQ ID NO 5
<211> LENGTH: 144
<212> TYPE: PRT
<213> ORGANISM: Helicobacter pylori

<400> SEQUENCE: 5

```
Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
                20                  25                  30

Phe Phe Asn Val His Lys Ala Thr Glu Glu Ile Tyr Glu Glu Phe Ala
            35                  40                  45

Asp Met Phe Asp Asp Leu Ala Glu Arg Leu Val Gln Leu Gly His His
        50                  55                  60

Pro Leu Val Thr Leu Ser Glu Ala Leu Lys Leu Thr Arg Val Lys Asp
65                  70                  75                  80

Glu Thr Lys Thr Ser Phe His Ser Lys Asp Ile Phe Lys Glu Ile Leu
                85                  90                  95

Gly Asp Tyr Lys His Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Glu Ala His Leu Ala
    130                 135                 140
```

<210> SEQ ID NO 6
<211> LENGTH: 144
<212> TYPE: PRT
<213> ORGANISM: Helicobacter pylori

<400> SEQUENCE: 6

```
Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
                20                  25                  30

Phe Phe Asn Val His Lys Ala Thr Glu Glu Ile Tyr Glu Glu Phe Ala
            35                  40                  45

Asp Met Phe Asp Asp Leu Ala Glu Arg Ile Val Gln Leu Gly His His
        50                  55                  60

Pro Leu Val Thr Leu Ser Glu Ala Ile Lys Leu Thr Arg Val Lys Glu
65                  70                  75                  80

Glu Thr Lys Thr Ser Phe His Ser Lys Asp Ile Phe Lys Glu Ile Leu
                85                  90                  95
```

```
Glu Asp Tyr Lys Tyr Leu Glu Lys Glu Phe Lys Glu Leu Ser Asn Thr
            100                 105                 110

Ala Glu Lys Glu Gly Asp Lys Val Thr Val Thr Tyr Ala Asp Asp Gln
        115                 120                 125

Leu Ala Lys Leu Gln Lys Ser Ile Trp Met Leu Gln Ala His Leu Ala
        130                 135                 140

<210> SEQ ID NO 7
<211> LENGTH: 39
<212> TYPE: DNA
<213> ORGANISM: Artificial Sequence
<220> FEATURE:
<223> OTHER INFORMATION: Novel Sequence

<400> SEQUENCE: 7
ctcgagctct agagggtatt aataatgaaa acattgaat                              39

<210> SEQ ID NO 8
<211> LENGTH: 29
<212> TYPE: DNA
<213> ORGANISM: Artificial Sequence
<220> FEATURE:
<223> OTHER INFORMATION: Novel Sequence

<400> SEQUENCE: 8
cccttaagct tttaagccaa atgagcttc                                         29

<210> SEQ ID NO 9
<211> LENGTH: 31
<212> TYPE: DNA
<213> ORGANISM: Artificial Sequence
<220> FEATURE:
<223> OTHER INFORMATION: Novel Sequence

<400> SEQUENCE: 9
tttttatgta taatagattc ataaatttga g                                      31
```